United States Patent
Singh et al.

(10) Patent No.: US 7,195,769 B2
(45) Date of Patent: Mar. 27, 2007

(54) PHARMACEUTICAL COMPOSITIONS OF ANTI-TUBERCULAR DRUGS AND PROCESS FOR THEIR PREPARATION

(75) Inventors: Amarjit Singh, New Delhi (IN); Rajesh Jain, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 192 days.

(21) Appl. No.: 10/110,134

(22) PCT Filed: Apr. 10, 2001

(86) PCT No.: PCT/IN01/00089

§ 371 (c)(1),
(2), (4) Date: Apr. 9, 2002

(87) PCT Pub. No.: WO02/11728

PCT Pub. Date: Feb. 14, 2002

(65) Prior Publication Data

US 2003/0072800 A1    Apr. 17, 2003

(30) Foreign Application Priority Data

Aug. 9, 2000   (IN) .......................... 720/DEL/2000

(51) Int. Cl.
*A61K 9/00* (2006.01)
*A61K 9/48* (2006.01)
*A61K 9/52* (2006.01)
*A61K 9/54* (2006.01)
*A61K 9/58* (2006.01)

(52) U.S. Cl. ............... 424/400; 424/451; 424/457; 424/458; 424/462; 424/463; 424/464; 424/468; 424/475; 424/480; 424/481; 424/482; 424/489; 424/490; 424/494; 424/496; 424/497

(58) Field of Classification Search ............... 424/400, 424/451, 452, 455, 457, 458, 459, 461, 462, 424/464, 465, 468, 470, 474, 475, 489, 490, 424/493, 494, 500, 725; 514/315, 924
See application file for complete search history.

(56) References Cited

U.S. PATENT DOCUMENTS 5,439,891 A * 8/1995 Kapil et al. .................... 514/31
6,264,991 B1 * 7/2001 Barrow et al. ............... 424/501

FOREIGN PATENT DOCUMENTS

| BE | 1 010 972 | 3/1999 |
| GB | 2 135 879 | 9/1984 |
| WO | 99 47123 | 9/1999 |

OTHER PUBLICATIONS

Shishoo et al (International Journal of Pharmaceutics 190 (1999), 109-123).*
Eier et al (Therapy of tuberculosis, Wien Med Wochenschr, 1994; 144(8-9): 186-8).*

* cited by examiner

Primary Examiner—Sreeni Padmanabhan
Assistant Examiner—Sharmila Gollamudi
(74) Attorney, Agent, or Firm—Oblon, Spivak, McClelland, Maier & Neustadt, P.C.

(57) ABSTRACT

A pharmaceutical composition of anti-tubercular drugs for oral use comprising Rifampicin and/or Isoniazid wherein the bioavailability of Rifampicin and/or other drugs is enhanced. Preferably the bioavailability of Rifampicin is enhanced by preventing its degradation caused by presence of Isoniazid. Rifampicin and/or Isoniazid may be present in delayed release and/or extended release form such that minimal amount of the drug is dissolved between pH 1 and 4. preferably delayed release of Rifampicin and/or Isoniazid is achieved by treating the drugs with pH sensitive polymers.

22 Claims, No Drawings

PHARMACEUTICAL COMPOSITIONS OF ANTI-TUBERCULAR DRUGS AND PROCESS FOR THEIR PREPARATION

Tuberculosis is a major problem largely of developing countries but lately emergence of Mycobacterium infections in HIV infected individuals is also on the rise in developed countries. The management of tuberculosis treatment is further complicated due to emergence of drug resistance. Drug resistance in tuberculosis is due to inappropriate prescribing or taking of medications, effectively resulting in monotherapy. To reduce the possibility of monotherapy, the World Health Organization (WHO) and the International Union Against Tuberculosis and Lung Diseases (IUATLD) have recommended that antitubercular drugs should be taken in combination (Fixed dose combination tablets for the treatment of tuberculosis, Report of an informal meeting held in Geneva 27 Apr. 1999, World Health Organization Communicable Diseases Cluster, 1999). A number of combinations of first line drugs containing rifampicin isoniazid pyrazinamide and ethambutol are in use This fixed dose combination (FDC) tablets provide a simple approach to delivering the correct number of drugs at the correct dosage as all the necessary drugs are combined in a single tablet. By altering the number of pills according to the patient's body weight, complete treatment is delivered without the need for calculation of dose. However, such FDC tablets are not free from disadvantages. The major issue is the adverse effect on bioavailability of rifampicin in presence of other drugs. Various researchers have worked on several aspects of this problem of FDC tablets and several recommendations are recorded in literature. WHO attributes that when rifampicin combined with the other drugs within the same formulation the bioavailability negatively affected if the manufacturing procedures are not strictly controlled. Against this background, WHO and IUATLD issued a joint statement in 1994 advising that only FDC tablets of good quality and proven bioavailability of rifampicin should be used in the treatment of tuberculosis (Anonymous; 1994; Tuber. Lung Dis.; 75: 180–181). There are several forthcoming articles in a special supplement of the International Journal of Tuberculosis and Lung disease devoted to the quality assurance of FDC tablets. These include a simplified protocol for assessing rifampicin bioavailability and its use in studies carried out in South Africa and India (Ellard, G. A.; 1999; Int. J. Tuberc. Lung Dis.; November 3; 11; Suppl. 3: S284–5; Mclleron, H. et al.; 1999; Int. J. Tuberc. Lung Dis.; November 3; 11; Suppl 3; S239–35; Panchagnula, R. et al.; 1999; Int. J. Tuberc. Lung Dis.; November 3; 11; Suppl 3; S336–42), high performance liquid chromatographic methods for assaying of rifampicin, isoniazid and Pyrazinamide (Smith, P. et al.; 1999; Int. J. Tuberc. Lung Dis.; November 3; 11; Suppl 3; S325–28) procedures for ensuring laboratory proficiency for rifampicin bioavailability studies (Ellard, G. A.; 1999; Int. J. Tuberc. Lung Dis.; November 3; 11; Suppl 3; S343–46) improved procedure of dissolution testing of rifampicin in presence of isoniazid (Shishoo, C. J. et al.; 1999; Int. J. Pharm.; November 10; 190 (1): 109–23) and a review of the pharmacology of rifampicin (Ellard, G. A. et al.; 1999; Int. J. Tuberc. Lung Dis.; November 3; 11 Suppl 3; S301–8: S317–21).

It has been reported that the poor absorption of rifampicin from combination products may be due to decomposition of the drug in acidic stomach conditions, which is accelerated in the presence of isoniazid (Shishoo, C. J. et al.; 1999; Int. J. Pharm.; November 10; 190 (1): 109–23; Singh, S. et al.; 2000; Pharm. Pharmacol. Commun.; 6: 491–494). The mechanism of this degradation was proposed by Singh et al. (Singh, S. et al.; 2000; Pharm. Pharmacol. Commun.; 6: 405–410). Studies revealed that the decomposition of rifampicin in acidic conditions in the absence of isoniazid stopped at the formation of 3-formylrifamycin, while the reaction in the presence of isoniazid proceeded to form a hydrazone between 3-formylrifamycin and isoniazid. Further, it was suggested that once 3-formylrifamycin is formed, it interacts with isoniazid to form the hydrazone, through a fast second order reaction. As hydrazone are unstable in acid conditions, 3-formylrifamycin and isoniazid are regenerated in a reversible manner through a slower first order reaction. In this complex reaction process, rifampicin is further degraded, while isoniazid is recovered.

Devani et al. (Devani, M. B. et al.; 1985; J. Pharm. Sci.; 74: 427–432) has also discussed kinetics of hydrazone formation from isoniazid in presence of reducing sugars.

None of the reports has suggested a pharmaceutical technological solution to the above problem. The inventors after careful experimentation and expenditure of considerable amount of mental faculties and time have found a novel way to solve the bioavailability problems of drugs in FDC tablets.

The invention described herein discloses compositions of anti-tubercular drugs where attempts have been made to prevent the loss in bioavailability of rifampicin in presence of isoniazid.

During experimentation the inventors have found that the degradation of rifampicin is pH dependent in presence of isoniazid. At pH around 1 the degradation is minimum and increases abruptly as pH ranges between 2 and 3. Thereafter, above pH 3 the degradation is minimal.

The pH of the gastric contents is normally between 1 and 3 which results in significant degradation of Rifampicin when administered orally alongwith other anti-tubercular agents, in particular Isoniazid.

This problem has been solved by controlling the release or dissolution of both the drugs in such a way that the release takes place at different locations inside the gastrointestinal tract without compromising the total bioavailability of either of the drugs. It means that the two drugs i.e. rifampicin and isoniazid do not come in contact with each other in solution state in the gastrointestinal tract thereby preventing the interaction. The composition may also include other known anti-tubercular drugs like Ethambutol Hydrochloride and Pyrazinamide.

The site-specific release of active ingredients has been achieved by various techniques like a) Controlling release of rifampicin and isoniazid at different locations in the gastrointestinal tract by use of pH sensitive materials b) Controlling dissolution of drugs by forming barrier coat and/or matrix with pH insensitive materials such that the contact of rifampicin and isoniazid in solution state is avoided.

c) Using different crystal forms of the drugs such that there is significant difference in dissolution rate of the drugs.

d) Modifying the surfactant action of rifampicin with use of materials like Methylpolysiloxane, natural and synthetic oils. Use of such materials reduces the surfactant action with corresponding reduction in solubility of rifampicin.

Preferably the drug is modified such that the release takes place at pH of approximately 5.0. At pH 5.0 the drug release takes place very rapidly such that there is no loss of bioavailability. Whereas the other drug or drugs are released in the more acidic (pH 1.0–3.0) environment of stomach.

Further, the invention discloses the Fixed Dose Combination of anti-tuberculosis drugs in oral suspension form. Suspension type dosage forms are of particular importance for fixed dose combination where the total amount of active ingredients of a single dose becomes very high. Such high doses cannot be filled into hard or soft gelatin capsules. Even compressed tablets become too big and are very difficult to swallow.

It has surprisingly been found in the present invention that it is possible to conveniently administer such high dose combinations of anti-tubercular drugs wherein one or more active ingredients may be present in extended or delayed release form, in the form of oral suspension leading to no loss of bioavailability of any of the actives. This has been achieved by making molecular dispersion of Rifampicin and/or isoniazid having pH dependent delayed release characteristics even when finely powdered. Such powders can be blended with other drugs and compressed into tablets or made into suspensions alongwith the other drugs. Another advantage is minimal increase in size of tablets which is serious problem for high dose drugs.

Further, the active ingredients may be in taste masked form. Such dosage forms will be highly desirable for treatment of tuberculosis in masses and reduction in the development of drug resistance which commonly occurs due to non compliance of existing type of dosage forms.

The active ingredients may be having barrier coating to prevent drug—drug/excipients interactions.

The suspension may be in ready-to-use form or to be reconstituted before use. Preferably the ready-to-use suspensions will have non-aqueous base/carrier. Suitable example of suspension bases include glycols and glycol derivatives; Propylene carbonate; glycerol; oils of animal, vegetable or mineral origin; medium chain triglycerides; transesterification products of natural vegetable oils with alkylene polyols; Esters of polyols with fatty acids.

Other ingredients of the suspension dosage form includes suspending agents, viscosity imparting agents, anti-caking agents, sweeteners, flavors, coloring agents and the like, known to persons skilled in the art.

The polymers used to modify the release of drugs may be natural, semi-synthetic, synthetic or man-modified. Suitable materials include cellulose and cellulose derivatives like microcrystalline cellulose, methyl cellulose, ethyl cellulose, hydroxypropylmethyl cellulose, hydroxypropyl cellulose, cellulose acetate phthalate, cellulose acetate, cellulose acetate butyrate, cellulose acetate propionate, cellulose acetate trimellitate, cellulose carboxymethyl ethers and their salts, hydroxypropyl methylcellulose phthalate, hydroxypropyl methylcellulose acetate succinate. Polyethylene; Polyquaternium-1; Polyvinyl acetate (homopolymer); Polyvinyl acetate phthalate; Propylene glycol alginate; PVM/MA copolymer; PVP/ dimethiconylacrylate/polycarbamyl/polyglycolester; PVP/dimethylamino ethylmethacry-late copolymer; PVP/dimethylaminoethylmethacrylate/polycarbamyl polyglycol ester; PVP/polycarbamyl polyglycol ester; PVP/VA copolymer Lanolin and lanolin derivatives, buffers, lipophilic materials like, fats, fatty acid glycerides, oleic acid, cholesterol, transesterification products of polyols with fatty acids, glyceryl monostearate, stearic acid, paraffins, beeswax, carnauba wax, tribehenin. Polyalkylene polyols like polyethylene glycols. Gelatin and gelatin derivatives. Alginates. Carbomers. Polycarbophils. Methacrylic acid copolymers. Carrageenans, pectins, chitosans, cyclodextrins, lecithins. Natural and synthetic gums containing galactomannans like xanthan gum, tragacanth, acacia, agar, guar gum, etc. Ion exchange resins like polacrilin pottasium, acrylic acid copolymers, sodium polystyrene sulphonate, polystyrene copolymers and the like.

Buffers like sodium dihydrogen orthophosphate, disodium hydrogen phosphate, dipotasium hydrogen phosphate, potassium dihydrogen orthophosphate, borate buffer, phthalate buffer, oxalate buffer and the like.

In another embodiment of the invention, the active ingredient may be present in micronized form to achieve faster absorption. Micronisation may be carried out by processes like air jet milling, ball mill and the like. The average particle size should be less than 5 microns.

Further the invention also discloses use of bioavailability enhancers like piperine and its derivatives, Ayurvedic preparations like trikatu alongwith the compositions of present invention may also help in increasing bioavailability.

The invention is further described with the help of following examples which should not be construed as limiting the scope of invention:

1. Microencapsulation of Rifampicin

| | |
|---|---|
| Cellulose Acetate Phthalate | 64 g |
| Rifampicin | 800 g |
| Polyethylene Glycol 4000 | 6.4 g |
| Water | 1200 ml |
| Hydrochloric Acid | 0.5 ml |
| Dichloromethane | 200 ml |
| Isopropyl Alcohol | 100 ml |

Procedure
1. Dissolve Cellulose Acetate Phthalate and Polyethylene Glycol 4000 in Isopropyl Alcohol & Dichloromethane mixture
2. Disperse rifampicin in water containing 0.5 ml of Hydrochloric Acid to make a slurry and keep on a water bath at 50° C.
3. Add CAP solution to the slurry with constant stirring.
4. Filter off the microcapsules and dry them.

The above mentioned microcapsules of Rifampicin may be blended with other anti-tubercular drugs and suitable excipients to formulate into tablets, capsules or suspension.

2. Microencapsulation of Rifampicin

| | |
|---|---|
| Sodium Alginate | 20 g |
| Rifampicin | 100 g |
| Calcium Chloride Solution | 5% w/v |
| Water | 500 ml |

Procedure
1. Dissolve Sodium Alginate in Purified Water.
2. Disperse rifampicin in above solution.
3. Add the above suspension dropwise to Calcium Chloride Solution with constant stirring.
5. Filter off the microcapsules and dry them.

The above mentioned microcapsules of Rifampicin may be blended with other anti-tubercular drugs and suitable excipients to formulate into tablets, capsules or suspension.

3. Preparation of Microcapsules of Rifampicin

| | |
|---|---|
| Rifampicin | 100 g |
| Ethyl Cellulose M20 | 100 g |
| Water | 600 ml |
| Dichloromethane | 300 ml |

Procedure
1. Dissolve Ethylcellulose in dichloromethane.
2. Disperse Rifampicin in water and keep in a water bath at 40° C.
3. Add solution of Ethylcellulose to drug slurry with constant stirring.
4. Filter off the microcapsules and wash with water and allow to air dry.

The above mentioned microcapsules of Rifampicin may be blended with other anti-tubercular drugs and suitable excipients to formulate into tablets, capsules or suspension.

4. Microspheres of Rifampicin

| | |
|---|---|
| Chitosan | 500 mg |
| Pluronic F68 | 2 g |
| Rifampicin | 10 mg |
| Sodium Tripolyphosphate (as 10% w/v solution in water) | 10 g |
| Water | 200 ml |

Procedure
1. Dissolve Chitosan in acetic acid containing Pluronic F-68 as surfactant.
2. Add 10 mg drug into Chitosan solution. Then add Sodium Tripolyphosphate dropwise with vigorous shaking. A cloudy suspension is formed as a result of crosslinking and precipitation of Chitosan microspheres.
3. Centrifuge the microspheres at 3000 rpm for 10 minutes and wash the pellets twice with deionized distilled water and dry them.

The above mentioned microspheres of Rifampicin may be blended with other anti-tubercular drugs and suitable excipients to formulate into tablets, capsules or suspension.

5. Microspheres of Rifampicin

| | |
|---|---|
| Rifampicin | 10 g |
| Agar Agar | 4 g |
| Citric Acid | 2 g |
| Water | 50 ml |
| Polyvinyl Alcohol | 15 g |
| Ethanol | 100 ml |

Procedure
1. Dissolve Citric Acid in Water and disperse Rifampicin, and Agar Agar in it with constant stirring.
2. Meanwhile, dissolve Polyvinyl Alcohol in Ethanol.
3. Add the aqueous solution to the alcoholic solution of Polyvinyl Alcohol with constant stirring.
4. Evaporate to dryness and separate the microspheres. Such microspheres can be formulated in suspension type dosage form as exemplified below:

| | |
|---|---|
| Rifampicin (In microspheres form as per example 5) | 0.200 g |
| Isoniazid (in taste masked form as per example 39) | 0.300 g |
| Pyrazinamide | 0.750 g |
| Ethambutol Hydrochloride(in taste masked form as per example 28) | 0.400 g |
| Aspartame | 0.025 g |
| Labrafac PG (Gattefosse, France) | 5.000 g |
| Corn oil | 3.000 g |
| Butylated Hydroxyanisole | 0.0015 g |
| Flavour | 0.097 g |

Procedure
1. Mix Labrafac PG and Corn oil and dissolve Butylated Hydroxyanisole in it with the aid of heat (40–50° C.).
2. Then add Rifampicin, Isoniazid, Pyrazinamide, Ethambutol Hydrochloride, Flavour and Aspartame to the bulk with stirring.

6. Bilayer Tablet

| | |
|---|---|
| Layer-I | |
| Rifampicin | 0.225 g |
| Hydroxypropyl methyl Cellulose Phthalate | 0.050 g |
| Isopropyl Alcohol | 2.000 g |
| Layer-II | |
| Isoniazid | 0.150 g |
| Pyrazinamide | 0.750 g |
| Ethambutol Hydrochloride | 0.400 g |
| Starch | 0.075 g |
| Water | 0.500 g |

Procedure
1. Granulate Rifampicin with solution of Hydroxypropylmethylcellulose Phthalate in Isopropyl Alcohol and dry them.
2. Separately, granulate Isoniazid, Pyrazinamide, Ethambutol Hydrochloride with Starch Paste in water and dry them.
3. Compress the granules into Bilayered tablets on a rotapress. Isoniazid (Layer-II) is immediately released. Rifampicin layer is released in delayed form in pH 5.5 and above.

7. Enteric Coated beads of Rifampicin

| | |
|---|---|
| Rifampicin | 0.5 Kg |
| Non-pareil beads | 1.2 Kg |
| Polyvinyl Pyrrolidone | 0.100 Kg |
| Isopropyl Alcohol | 7.00 L |
| Eudragit L100 | 0.40 Kg |
| Acetone | 6.00 L |
| Water | 1.00 L |
| Triethyl Citrate | 0.04 Kg |

Procedure
1. Prepare The enteric coated beads of Rifampicin using fluid bed coater.
2. Spray dispersion of Rifampicin and Polyvinyl Pyrrolidone in Isopropyl Alcohol onto the fluidized non pareil beads.
3. Spray dispersion of Eudragit L100 and Triethyl Citrate in water/Acetone mixture on the rifampicin beads.

Such beads may be used in conjunction with other drugs to make formulations as exemplified below:

| | | |
|---|---|---|
| (i) | Rifampicin (In enteric coated bead form as per example 7) | 600 mg |
| (ii) | Isoniazid | 150 mg |

Mix (i) and (ii) and fill in hard gelatin capsules, or mix (i) and (ii) with suitable lubricants and diluent like lactose, microcrystalline cellulose and compress into tablets or fill in hard carpsules.

8. Rifampicin Granules (Delayed Release)

| | |
|---|---|
| Rifampicin | 9.00 Kg |
| Eudragit L100 (Rohm Pharma, Germany) | 1.00 Kg |
| Acetone | 3.0 L |
| Water | 0.5 L |

Procedure
1. Dissolve Eudragit L 100 in mixture of acetone and water.
2. Granulate Rifampicin in a rapid mixer granulator with the above solution. Sift the wet mass through 10 mesh screen and dry.
3. After drying the granules, sift the granules through 30 mesh screen. Such granules may be added to a oral suspension or capsule or compressed into tablets alongwith other active agents and excipients.

The above mentioned granules of Rifampicin may be blended with other anti-tubercular drugs and suitable excipients to formulate into tablets, capsules or suspension.

9. Molecular Dispersion of Rifampicin with Enteric (Delayed Release) Effect

| | |
|---|---|
| Rifampicin | 9.00 Kg |
| Eudragit L100 (Rohm Pharma, Germany) | 0.50 Kg |
| Cellulose Acetate Phthlate | 1.00 Kg |
| Isopropyl Alcohol | 5.0 L |
| Methylene chloride | 10.0 L |

Procedure
1. Dissolve Eudragit L 100 and Cellulose Acetate Phthlate in mixture of Isopropyl Alcohol and Methylene Chloride separately. Mix both the solutions.
2. Dissolve Rifampicin in Methylene Chloride and add to the above solution and mix for one hour.
3. Evaporate the solvents on a water bath and pass the residue through a sieve of mesh size 100.

The above mentioned powder of Rifampicin has almost no release in acid stage i.e. pH 1–3 for upto 2 hours. Whereas above pH 5.5 more than 85% of drug is released in about 45 minutes. This powder may be blended with other anti-tubercular drugs and suitable excipients to formulate into tablets, capsules or suspension. Upon compression, there is no change in release of rifampicin during acid stage.

10. Molecular Dispersion of Rifampicin with Enteric (Delayed Release) Effect

| | |
|---|---|
| Rifampicin | 8.00 Kg |
| Eudragit L100 (Rohm Pharma, Germany) | 0.50 Kg |
| Polyvinyl Acetate Phthalate | 0.75 Kg |
| Isopropyl Alcohol | 4.0 L |
| Dichloromethane | 8.0 L |

Procedure
1. Dissolve Eudragit L 100 and Polyvinyl Acetate Phthalate are in mixture of Isopropyl Alcohol and Dichloromethane separately. Mix both the solutions.
2. Dissolve Rifampicin was dissolved in Dichloromethane and add to the above solution and mix for one hour.
3. Evaporate the solvents on a water bath and pass the through a sieve of mesh size 100.

The above mentioned powder of Rifampicin may be blended with other anti-tubercular drugs and suitable excipients to formulate into tablets, capsules or suspension.

11. Molecular Dispersion of Rifampicin with Enteric (Delayed Release) Effect

| | |
|---|---|
| Rifampicin | 2.00 Kg |
| Shellac | 0.10 Kg |
| Isopropyl Alcohol | 1.0 L |
| Methylene Chloride | 2.0 L |

Procedure
1. Dissolve Shellac in a mixture of Isopropyl Alcohol and Methylene Chloride separately.
2. Dissolve Rifampicin in Methylene chloride and add to the above solution and mix for two hours.
3. Evaporate the solvents on a water bath and pass the residue through a sieve of mesh size 100.

The above mentioned powder of Rifampicin may be blended with other anti-tubercular drugs and suitable excipients to formulate into tablets, capsules or suspension.

12. Rifampicin Granules (Delayed Release)

| | |
|---|---|
| Rifampicin | 2.00 Kg |
| Eudragit L 30D | 0.20 Kg |
| Purified Water | 0.50 L |

Procedure
1. Dilute Eudragit L 30 D with Purified Water.
2. Granulate Rifampicin with the above solution in a mass mixer for 1.5–2.0 h.
3. Pass the wet mass through multimill and dry the granules.

An oral suspension using such granules is described below:

Oral Suspension

| | |
|---|---|
| Rifampicin | 225 mg |
| (In delayed release granule form as per example 12) | |
| Isoniazid | 150 mg |
| (In taste masked form for taste masking as per example 39) | |
| Ethambutol Hydrochloride | 400 mg |
| (in ion-exchange complexed form for taste masking as per example 28) | |
| Pyrazinamide | 750 mg |
| Colloidal Silicon Dioxide | 100 mg |
| Aspartame | 20 mg |
| Flavour | q.s |
| Medium Chain Triglyceride | q.s to 10 ml |

Procedure

Disperse Colloidal Silicon Dioxide, Aspartame in Medium chain triglyceride. Add rifampicin granules, Isoniazid, Ethambutol Hydrochloride and Pyrazinamide and flavour with stirring.

13. FDC Formulation Containing Piperine as Absorption Enhancer

| | |
|---|---|
| Rifampicin | 225 mg |
| (In delayed release granule form as per example 12) | |
| Piperine | 60 mg |
| Isoniazid | 150 mg |
| (In taste masked form for taste masking as per example 39) | |
| Ethambutol Hydrochloride | 400 mg |
| (in ion-exchange complexed form for taste masking as per example 28) | |
| Pyrazinamide | 750 mg |
| Colloidal Silicon Dioxide | 100 mg |
| Aspartame | 20 mg |
| Flavour | q.s |
| Medium Chain Triglyceride | q.s to 10 ml |

Procedure

Disperse Colloidal Silicon Dioxide, Aspartame in Medium chain triglyceride. Add rifampicin granules, Piperine, Isoniazid, Ethambutol and Pyrazinamide and flavour with stirring.

14. pH Sensitive Fast Release Granules of Rifampicin

| | |
|---|---|
| Core | |
| Rifampicin | 20 parts |
| Low substituted Hydroxypropyl Cellulose | 52 parts |
| Lactose | 13 parts |
| Hydroxypropyl Cellulose | 5 parts |
| Alcohol (Ethanol 95% v/v) | 20 parts |
| Film | |
| Eudragit L 100 | 5.5 parts |
| Isopropyl Alcohol | 60.2 parts |
| Acetone | 33.5 parts |
| Dibutyl Phthalate | 0.8 parts |

Procedure
1. Mix Rifampicin, Low substituted Hydroxypropyl Cellulose, Lactose.
2. Granulate the above bulk with alcoholic solution of Hydroxypropyl Cellulose.
3. Dry the granules and sift through mesh 60.
4. Coat the granules with enteric film forming solution of Eudragit L 100 and Dibutyl Phthalate in Isopropyl Alcohol and Acetone using fluid bed coater.

Such granules may be used to make capsules, tablets or oral suspension.

15. Millispheres of Rifampicin

| | |
|---|---|
| Phase-I | |
| Rifampicin | 10 g |
| Sodium Alginate | 20 g |
| Water | 90 g |
| Phase-II | |
| Chitosan | 5 g |
| Calcium Chloride | 5 g |
| Water | 200 ml |

Prepare Phase-I solution by dispersing Rifampicin and Sodium Alginate in Water. Dissolve Chitosan, Calcium Chloride in water to prepare Phase-II. Add Phase-I dropwise with stirring to Phase-II. Soft millispheres of rifampicin are formed. Separate by filteration and dry under vacuum.

Such millispheres may be used to formulate oral suspension dosage form alongwith other anti-tubercular agents.

16. Rifampicin in Lipophilic Matrix

| | |
|---|---|
| Rifampicin | 5.0 Kg |
| Glyceryl Monostearate | 2.0 Kg |
| Poloxamer 188 | 0.1 Kg |
| Lactose | 2 Kg |
| Ethyl Cellulose | 0.5 Kg |
| Alcohol (Ethanol 95% v/v) | 2.0 L |

Procedure
1. Dissolve Glyceryl Monostearate and Poloxamer in Alcohol and heat up to 70° C. so as to obtain a clear solution.
2. Add drug to the bulk and cool.
3. Evaporate the alcohol and granulate the residue with Lactose as diluents and Ethyl Cellulose as binder.

Such granules may be used to formulate a tablet, capsule, dosage form or oral suspension dosage form alongwith other anti-tubercular agents.

17. Rifampicin in Carbomer Matrix

| | |
|---|---|
| Rifampicin | 5.0 Kg |
| Carbomer (Carbopol 934P, BF Goodrich) | 1.0 Kg |
| Lactose | 5.0 Kg |
| Ethyl Cellulose | 0.5 Kg |
| Acetone | 2.0 L |
| Alcohol (Ethanol 95% v/v) | 10.0 L |
| Water | 5.0 L |

Procedure
1. Dissolve the drug in alcohol and Carbopol in water. Mix both the solution and keep aside for one hour.
2. Evaporate the solvents and pulverised the mass into powder and granulate with Lactose as diluent and Ethyl Cellulose in Acetone as binder.

Such granules may be used to formulate a tablet, capsule, dosage form or oral suspension dosage form alongwith other anti-tubercular agents.

18. Mesosomes of Rifampicin

| | |
|---|---|
| Rifampicin | 2.0 Kg |
| Glyceryl Monostearate | 1.0 Kg |
| Palmitic Acid | 0.5 Kg |
| Tween 60 | 0.1 Kg |
| Water | 5.0 L |

Melt Glyceryl Monostearate and Palmitic Acid in a water bath and disperse drug in it Pour the molten mass to hot purified water containing Tween 60 under stirring. Then add this to ice chilled water with continuous stirring. Filter the mesosomes and air dry them.

The above mentioned mesosomes of rifampicin may be blended with anti tubercular drugs and suitable excipients to formulate into tablets, capsules or suspensions 19. Tablet-in-Tablet Formulation (Rifampicin in Delayed Release Form)

| Core tablet | Per tablet |
|---|---|
| Rifampicin | 225 mg |
| Starch | 20 mg |
| Lactose | 28 mg |
| Water | — |
| Magnesium Stearate | 10 mg |
| Sodium Lauryl sulphate | 10 mg |
| Sodium Starch Glycollate | 30 mg |

Pass Rifampicin and Lactose through sieve and granulate with Starch Paste and pass through multimill. Dry the granules at 50° to 60° C. and pass through sieve of mesh size 18. Pass Sodium Starch Glycollate, Sodium Lauryl Sulphate and Magnesium Stearate through sieve of mesh size 40 and mix with the dried granules and compress.

Enteric Coating of Rifampicin Tablets (Batch Size 2.0 Kg)

| Eudragit L 100 | 88.00 g |
|---|---|
| Purified Talc | 20.00 g |
| Triethyl Citrate | 18.00 g |
| Dichloromethane | 1.30 L |
| Isopropyl Alcohol | 0.60 L |

Dissolve Eudragit L 100 in Isopropyl Alcohol and dichloromethane mixture. Add Triethyl Citrate and Talc to the above bulk and mix for 45 minutes. Coat the tablets to a weight build up of 6–8% w/w.

Outer Tablet

| Pyrazinamide | 750 mg |
|---|---|
| Ethambutol Hydrochloride | 400 mg |
| Isoniazid | 150 mg |
| Magnesium Stearate | 10 mg |
| Sodium Starch Glycollate | 30 mg |
| Lactose | 65 mg |
| Povidone | 50 mg |
| Purified Water | — |

Pass Pyrazinamide, Ethambutol Hydrochloride, Isoniazid and lactose through a sieve and granulate with Povidone solution in water. Pass the wet mass through multimill and dry the granules 50–60° C. Pass dried granules through sieve of mesh size 16. Pass Magnesium Stearate and Sodium Starch Glycollate through sieve of mesh size 60 and mix with dried granules. Compress into tablets alongwith the Rifampicin enteric coated tablets in between.

Film Coating of Outer Tablets (Batch Size 2.0 Kg)

| Hypromellose | 40.00 g |
|---|---|
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

20. Tablet-in-Tablet Formulation (Isoniazid in Delayed Release Form)

| Isoniazid | 150 mg |
|---|---|
| Lactose | 30 mg |
| Starch | 5 mg |
| Water | — |
| Magnesium Stearate | 3 mg |
| Purified Talc | 3 mg |

Pass Isoniazid and Lactose through sieve and granulate with Starch paste and pass through multimill. Dry the granules at 50° to 60° C. and pass through sieve of mesh size 18. Pass Magnesium Stearate and Talc through sieve of mesh size 60 and mix with the dried granules and compress.

Enteric Coating of Isoniazid Tablets (Batch Size 2.0 Kg)

| Hydroxypropylmethyl Cellulose Phthlate | 80.00 g |
|---|---|
| Purified Talc | 25.00 g |
| Dibutyl Sebacate | 15.00 g |
| Dichloromethane | 1.30 L |
| Isopropyl Alcohol | 0.60 L |

Dissolve Hydroxypropylmethyl Cellulose Phthlate in Isopropyl Alcohol and Dichloromethane mixture. Add Dibutyl Sebacate and Talc to the above bulk and mix for 45 minutes. Coat the tablets to a weight build up of 4–6% w/w.

Outer Tablet

| Pyrazinamide | 750 mg |
|---|---|
| Ethambutol Hydrochloride | 400 mg |
| Rifampicin | 225 mg |
| Lactose | 70 mg |
| Magnesium Stearate | 10 mg |
| Sodium Starch Glycollate | 15 mg |
| Povidone | 30 mg |
| Purified Water | — |

Pass Pyrazinamide, Ethambutol Hydrochloride, Rifampicin and Lactose through a sieve and granulate with Povidone solution in water. Pass the wet mass through multimill and dry the granules at 50–60° C. Pass the dried granules through sieve of mesh size 16. Pass Magnesium Stearate and Sodium Starch Glycollate through sieve of mesh size 60 and mix with dried granules. Compress the tablets alongwith the Isoniazid enteric coated tablets in between.

Film Coating of Outer Tablets (Batch Size 2.0 Kg)

| Hypromellose | 40.00 g |
|---|---|
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

21. Tablet Formulation Containing Isoniazid in Delayed Release Form

| Core tablet | Per tablet |
| --- | --- |
| Isoniazid | 150 mg |
| Lactose | 30 mg |
| Eudragit L 30 D (Rohm Pharma, Germany) | 50 mg |
| Purified Water | — |

Pass Isoniazid and Lactose through sieve and granulate with aqueous dispersion of diluted Eudragit L 30 D in a mass mixer for at least 2 hours. Pass the granules through sieve and dry them.

Outer Tablet

| | |
| --- | --- |
| Isoniazid Enteric Coated equivalent to | 230 mg |
| Isoniazid | 150 mg |
| Ethambutol Hydrochloride | 400 mg |
| Pyrazinamide | 750 mg |
| Rifampicin | 225 mg |
| Lactose | 20 mg |
| Magnesium Stearate | 10 mg |
| Sodium Starch Glycollate | 35 mg |
| Povidone | 30 mg |
| Purified Water | — |

Pass Pyrazinamide, Ethambutol Hydrochloride, Rifampicin and Lactose through a sieve and granulate with Povidone solution in water. Pass the wet mass through multimill and dry the granules at 50–60° C. Pass the dried granules through sieve of mesh size 16. Mix Magnesium Stearate, Sodium Starch Glycollate and Isoniazid granules with above granules and compress.

Film Coating of Tablets (Batch Size 2.0 Kg)

| | |
| --- | --- |
| Hypromellose | 40.00 g |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

22. Molecular Dispersion of Isoniazid with Enteric (Delayed Release) Effect

| | |
| --- | --- |
| Isoniazid | 10.00 Kg |
| Eudragit L100 (Rohm Pharma, Germany) | 2.00 Kg |
| Isopropyl Alcohol | 5.0 L |
| Alcohol (Ethanol 95% v/v) | 15.0 L |

Dissolve Eudragit L 100 in Isopropyl Alcohol. Dissolve Isoniazid in Alcohol and add to the above solution and mix for one hour. Evaporate the solvents on a water bath and pass the residue through a sieve of mesh size 100.

The above powder may be used to make capsules, tablets or oral suspension.

23. Molecular Dispersion of Isoniazid with Enteric (Delayed Release) Effect

| | |
| --- | --- |
| Isoniazid | 8.00 Kg |
| Eudragit L100 (Rohm Pharma, Germany) | 1.00 Kg |
| Polyvinyl Acetate Phthalate | 0.75 Kg |
| Isopropyl Alcohol | 4.0 L |
| Alcohol (Ethanol 95 % v/v) | 15.0 L |

Dissolve Eudragit L 100 and Polyvinyl Acetate Phthalate in Isopropyl Alcohol separately. Mix both the solutions and dissolve Isoniazid in Alcohol and add to the above solution and mix for one hour. Evaporate the solvents on a water bath and pass the residue through a sieve of mesh size 100.

The above powder may be used to make capsules, tablets or oral suspension.

24. Molecular Dispersion of Isoniazid with Enteric (Delayed Release) Effect

| | |
| --- | --- |
| Isoniazid | 2.00 Kg |
| Shellac | 0.10 Kg |
| Isopropyl Alcohol | 1.0 L |
| Alcohol (Ethanol 95 % v/v) | 5.0 L |

Dissolve Shellac in a Isopropyl Alcohol. Dissolve Isoniazid in Alcohol and add to the above solution and mix for two hours. Evaporate the solvents on a water bath and pass the residue through a sieve of mesh size 100.

An oral suspension using above molecular dispersion is described below:

Oral Suspension

| | |
| --- | --- |
| Isoniazid | 150 mg |
| (In delayed release molecular dispersion form as per example 23) | |
| Rifampicin | 225 mg |
| Ethambutol Hydrochloride | 400 mg |
| (in ion-exchange complexed form for taste masking as per example 28) | |
| Pyrazinamide | 750 mg |
| Colloidal Silicon Dioxide | 100 mg |
| Aspartame | 20 mg |
| Flavour | q.s |
| Medium Chain Triglyceride | q.s to 10 ml |

Disperse Colloidal Silicon Dioxide, Aspartame in Medium chain Triglyceride. Add Isoniazid powder, Rifampicin, Ethambutol Hydrochloride and Pyrazinamide and flavour with stirring.

26. Enteric Coated Beads of Isoniazid

| | |
| --- | --- |
| Isoniazid | 1.0 Kg |
| Non-pareil beads | 3.0 Kg |
| Polyvinyl Pyrrolidone | 0.20 Kg |

|   |   |
|---|---|
| Isopropyl Alcohol | 14.00 L |
| Eudragit L100 | 0.80 Kg |
| Acetone | 12.00 L |
| Water | 2.00 L |
| Triethyl Citrate | 0.10 Kg |

Procedure

The enteric coated beads of Isoniazid are manufactured using fluid bed coater. Spray dispersion of Isoniazid and Polyvinyl Pyrrolidone in Isopropyl Alcohol onto the fluidized non pareil beads. Further coat dispersion of Eudragit L100 and Triethyl Citrate in water/Acetone mixture on the Isoniazid beads.

Such beads may be used in conjunction with other drugs to make formulation as examplified below:

|   |   |
|---|---|
| (i) Isoniazid | 150 mg |
| (In enteric coated bead form as per example 25) | |
| (ii) Rifampicin | 600 mg |

Mix (i) and (ii) and fill in hard gelatin capsules, or mix (i) and (ii) with suitable lubricants and diluent like lactose, microcrystalline cellulose and compress into tablets 26. Isoniazid in Lipophilic Matrix

|   |   |
|---|---|
| Isoniazid | 5.0 Kg |
| Glyceryl Monostearate | 2.0 Kg |
| Poloxamer 188 | 0.1 Kg |
| Lactose | 2 Kg |
| Ethyl Cellulose | 1.0 Kg |
| Alcohol (Ethanol 95% v/v) | 10.0 L |

Dissolve Glyceryl Monostearate and Poloxamer in Alcohol and heat up to 70° C. so as to obtain a clear solution. Add drug to the bulk and cool. Evaporate the Alcohol and granulate the mixture with Lactose as diluents and Ethyl Cellulose as binder.

The above mentioned granules of Isoniazid may be blended with other anti-tubercular drugs and suitable excipients to formulate into tablets, capsules or suspension.

27. Bilayer Tablet Containing Isoniazid in Extended Release Form

|   |   |
|---|---|
| Layer-I | |
| Isoniazid | 0.150 g |
| Hydroxypropylmethyl Cellulose K4M | 0.050 g |
| Isopropyl Alcohol | 2.000 g |
| Layer-II | |
| Rifampicin | 0.225 g |
| Ethambutol Hydrochloride | 0.400 g |
| Pyrazinamide | 0.750 g |
| Starch | 0.075 g |
| Water | 0.500 g |

Granulate Isoniazid with solution of Hydroxypropylmethyl Cellulose K4M in Isopropyl Alcohol and dry. Granulate Rifampicin, Ethambutol Hydrochloride and Pyrazinamide with Starch paste in water and dry. Compress into bilayered tablets on a rotapress. Rifampicin (Layer-II) is immediately released. Isoniazid layer is released in delayed form.

28. Ethambutol Hydrochloride in Taste Masked Form Using Complexation

|   |   |
|---|---|
| Ethambutol Hydrochloride | 1.0 Kg |
| Polystyrene Copolymer | 2.0 Kg |
| Water | 5.0 L |

Disperse Polystyrene copolymer in Water and add Ethambutol Hydrochloride to it with constant stirring. Continue stirring for two hours and filter the complex and dry.

The above complex may be included in a tablet, capsule or suspension dosage form for taste masked and delayed release Isoniazid suspension containing other antitubercular drugs.

29. Tablet-in-Tablet Formulation (Rifapentine in Delayed Release Form)

| Core tablet: | Per tablet |
|---|---|
| Rifapentine | 150 mg |
| Microcrystalline Cellulose | 75 mg |
| Starch | 10 mg |
| Water | — |
| Disodium Edetate | 3 mg |
| Magnesium Stearate | 5 mg |
| Purified Talc | 2 mg |
| Sodium Lauryl Sulphate | 5 mg |

Pass Rifapentine and Microcrystalline Cellulose through sieve and granulate the mass with Starch paste and pass through multimill. Dry the granules at 50° to 60° C. and pass through sieve of mesh size 18. Pass Magnesium Stearate, Disodium Edetate, Sodium Lauryl Sulphate and Purified Talc through sieve of mesh size 60 and mix with the dried granules and compress.

Enteric Coating of Rifapentine Tablets (Batch Size 2.0 Kg)

|   |   |
|---|---|
| Cellulose Acetate Phthlate | 85.00 g |
| Purified Talc | 20.00 g |
| Polyethylene Glycol 400 | 10.00 g |
| Dichloromethane | 1.33 L |
| Isopropyl Alcohol | 0.66 L |

Dissolve Cellulose Acetate Phthlate in Isopropyl Alcohol and Dichloromethane mixture. Add Polyethylene Glycol 400 and Talc to the above bulk and mix for 45 minutes. Coat the tablets to a weight build up of 4–6% w/w.

|   |   |
|---|---|
| Pyrazinamide | 750 mg |
| Ethambutol Hydrochloride | 400 mg |
| Isoniazid | 150 mg |
| Lactose | 60 mg |
| Magnesium Stearate | 20 mg |
| Sodium Starch Glycollate | 30 mg |
| Starch | 20 mg |
| Purified Talc | 5 mg |
| Purified Water | — |

Pass Pyrazinamide, Ethambutol Hydrochloride, Isoniazid and Lactose through a sieve and granulate with Starch Paste prepared in Purified Water. Pass the wet mass through multimill and dry the granules at 50–60° C. Pass the dried granules through sieve of mesh size 16. Pass Magnesium Stearate, Purified Talc and Sodium Starch Glycollate through sieve of mesh size 60 and mix with dried granules. Compress the tablets alongwith the Rifapentine enteric coated tablets in between.

Film Coating of Outer Tablets (Batch Size 2.0 Kg)

| Hypromellose | 40.00 g |
|---|---|
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

30. Effervescent Tablet/Granules (Rifampicin in Delayed Release Form).

| Rifampicin Enteric Coated Granules | 225 mg |
|---|---|
| Equivalent to Rifampicin (from example no. 8) | |
| Pyrazinamide | 750 mg |
| Isoniazid | 150 mg |
| Ethambutol Hydrochloride | 400 mg |
| Anhydrous Citric Acid | 340 mg |
| Sodium Bicarbonate | 360 mg |
| Anhydrous Sodium Carbonate | 20 mg |
| Povidone | 50 mg |
| Polyethylene Glycol 6000 | 25 mg |
| Sodium Benzoate | 20 mg |
| Aspartame | 20 mg |
| Magnesium Stearate | 7.5 mg |
| Sodium Lauryl Sulphate | 2.5 mg |
| Flavour | 25 mg |
| Isopropyl Alcohol | — |
| Dichloromethane | — |

Pass Pyrazinamide, Ethambutol Hydrochloride, Isoniazid through a sieve of mesh size 40. Pass Anhydrous Citric Acid, Sodium Bicarbonate and Anhydrous Sodium Carbonate through sieve of mesh size 100 and mix with the above bulk. Dissolve Povidone in Isopropyl Alcohol and Dichloromethane mixture and granulate the bulk with binder solution and pass the wet mass through multimill and dry the granules. Pass the dried granules through sieve of mesh size 16. Pass Magnesium Stearate, Polyethylene Glycol 6000, Aspartame, Sodium Benzoate, Sodium Lauryl Sulphate and flavour through sieve and mix with dried granules.

The above effervescent granules can be dispensed in a pouch/sachets or in a tablet dosage form. All the processing is carried in dehumidified conditions at relative humidity not more than 20% and temperature not more than 25° C.

31. Buffered Tablets Containing Rifampicin in Delayed Release Form

| Rifampicin delayed release granules equivalent to Rifampicin (from example no. 8) | 225 mg |
|---|---|
| Pyrazinamide | 750 mg |
| Isoniazid | 150 mg |
| Ethambutol Hydrochloride | 400 mg |

-continued

| Lactose | 22.5 mg |
|---|---|
| Starch | 30 mg |
| Magnesium Stearate | 7.5 mg |
| Sodium Starch Glycollate | 30 mg |
| Sodium Carbonate | 100 mg |
| Purified Water | — |

Pass Pyrazinamide, Ethambutol Hydrochloride, Isoniazid and Lactose through a sieve of mesh size 40. Granulate the above bulk with Starch paste containing water and pass the wet mass through multimill and dry the granules. Pass Magnesium Stearate, Sodium Starch Glycollate and Sodium Carbonate through sieve and mix with dried granules, rifampicin enteric coated granules and compress.

| Film Coating of tablets (Batch Size 2.0 Kg) | |
|---|---|
| Hypromellose | 40.00 g |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

32. Hard Gelatin Capsule Formulation Containing Isoniazid in Delayed Release Form.

| | Per Capsule |
|---|---|
| Isoniazid Enteric Coated tablets (example no. 20) | 200 mg ≅ Tab. |
| Rifampicin (Compacted) | 225 mg |
| Sodium Lauryl Sulphate | 3 mg |

Pass Rifampicin through sieve of mesh size 22 and mix with the Sodium Lauryl Sulphate previously passed through sieve of mesh size 40. Fill 228 mg of above powder and one Isoniazid enteric coated tablet in each empty hard gelatin capsules size "0".

33. Molecular Dispersion of Rifabutin with Enteric (Delayed Release) Effect

| Rifabutin | 10.00 Kg |
|---|---|
| Eudragit L100 (Rohm Pharma, Germany) | 2.50 Kg |
| Isopropyl Alcohol | 6.0 L |
| Dichloromethane | 17.0 L |

Dissolve Eudragit L 100 in a mixture of Isopropyl Alcohol and Dichloromethane. Disslove Rifabutin in Dichloromethane and add to the above solution and mix for one hour. Evaporate the solvents on a water bath and pass the residue through a sieve of mesh size 100.

The above mentioned powder of Rifabutin may be blended with other anti-tubercular drugs and suitable excipients to formulate into tablets, capsules or suspension.

34. Tablet Formulation Containing Rifabutin in Delayed Release Form

|  | Per tablet |
| --- | --- |
| Rifabutin | 150 mg |
| (In delayed release molecular dispersion form as per example 33) | |
| Isoniazid | 150 mg |
| Ethambutol Hydrochloride | 400 mg |
| Pyrazinamide | 750 mg |
| Lactose | 135 mg |
| Magnesium Stearate | 20 mg |
| Sodium Starch Glycollate | 30 mg |
| Starch | 30 mg |
| Purified Talc | 5 mg |

Pass Pyrazinamide, Ethambutol Hydrochloride, Isoniazid and Lactose through a sieve and granulate with Starch Paste prepared in Purified Water. Pass the wet mass through multimill and dry the granules at 50–60° C. Pass the dried granules through sieve of mesh size 16. Mix Magnesium Stearate, Sodium Starch Glycollate, Purified Talc and Rifabutin delayed release powder with dried granules and compress.

Film Coating of Tablets (Batch Size 2.0 Kg)

| Hydroxypropyl Methycellulose | 40.00 g |
| --- | --- |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hydrxypropylmethylcellulose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

36. Powder for Reconstitution Containing Isoniazid in Delayed Release Form.

| Isoniazid | 150 mg |
| --- | --- |
| (In delayed released molecular dispersion form as per example 22) | |
| Rifampicin | 225 mg |
| Ethambutol Hydrochloride | 400 mg |
| (In ion exchange complexed form for taste masking as per example 28) | |
| Pyrazinamide | 750 mg |
| Methyl Hydroxybenzoate | 5 mg |
| Sodium Metabisulphite | 10 mg |
| Sweetening Agent | q.s. |
| Xanthan Gum | 20 mg |
| Flavour | q.s. |

Pass Pyrazinamide, Ethambutol Hydrochloride, Isoniazid delayed release powder, Rifampicin, Methyl Hydroxybenzoate, and Sodium Metabisulphite through sieve of mesh size 60. Pass Xanthan Gum and Sweetening Agent through a sieve of mesh size 100. Mix both the bulks and fill in amber coloured glass bottles.

36. Powder for Reconstitution Containing Rifampicin in Delayed Release Form.

| Rifampicin in delayed release molecular dispersion form equivalent to Rifampicin (as per example 9) | 225 mg |
| --- | --- |
| Isoniazid | 150 mg |
| (in taste masked form as per example 39) | |
| Ethambutol Hydrochloride | 400 mg |
| (In ion exchange complexed form for taste masking as per example 28) | |
| Pyrazinamide | 750 mg |
| Methyl Hydroxybenzoate | 5 mg |
| Sodium Metabisulphite | 10 mg |
| Sweetening Agent | q.s. |
| Xanthan Gum | 20 mg |
| Flavour | q.s. |

Pass Pyrazinamide, Ethambutol Hydrochloride, Isoniazid, Rifampicin delayed release powder, Methyl Hydroxybenzoate, and Sodium Metabisulphite through sieve of mesh size 60. Pass Xanthan gum and Sweetening Agent through a sieve of mesh size 100 and mix both the bulks and fill in amber coloured glass bottles.

37. An Anti Tubercular Formulation in Kit Form.

The kit contains
(A) One tablet of Isoniazid 150 mg (Enteric coated)
(B) One tablet containing Rifampicin, Ethambutol Hydrochloride and Pyrazinamide (Film coated)

(A) Isoniazid Tablets 150 mg (Enteric coated)

|  | Per tablet |
| --- | --- |
| Isoniazid | 150 mg |
| Lactose | 30 mg |
| Starch | 5 mg |
| Water | — |
| Magnesium Stearate | 3 mg |
| Purified Talc | 3 mg |

Pass Isoniazid and Lactose through sieve and granulate the mass with Starch paste and pass through multimill. Dry the granules at 50° to 60° C. and pass through sieve of mesh size 18. Pass Magnesium Stearate and Talc through sieve of mesh size 60 and mix with the dried granules and compress.

Enteric Coating of Isoniazid Tablets (Batch Size 2.0 Kg)

| Eudragit L 100 | 80.00 g |
| --- | --- |
| Purified Talc | 25.00 g |
| Triethyl Citrate | 15.00 g |
| Dichloromethane | 1.30 L |
| Isopropyl Alcohol | 0.60 L |

Dissolve Eudragit L 100 in Isopropyl Alcohol and Dichloromethane mixture. Add Triethyl Citrate and Talc to the above bulk and mix for 45 minutes. Coat the tablets to a weight build up of 4–6% w/w.

(B) Rifampicin, Ethambutol Hydrochloride and Pyrazinamide Tablets (Film Coated)

|  | Per Tablet |
| --- | --- |
| Pyrazinamide | 750 mg |
| Ethambutol Hydrochloride | 400 mg |
| Rifampicin | 225 mg |
| Lactose | 50 mg |
| Magnesium Stearate | 15 mg |
| Talc | 6 mg |
| Starch | 19 mg |
| Crospovidone | 35 mg |
| Purified Water | — |

Pass Pyrazinamide, Ethambutol Hydrochloride, Rifampicin and Lactose through a sieve and granulate with Starch paste prepared in Purified Water. Pass the wet mass through multimill and dry the granules at 50–60° C. Pass dried granules through sieve of mesh size 16. Pass Magnesium Stearate, Purified Talc and Crospovidone through sieve of mesh size 60 and mix with dried granules and compress.

| Film Coating of tablets (Batch Size 2.0 Kg) | |
| --- | --- |
| Hypromellose | 40.00 g |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

38. An Anti Tubercular Formulation in Kit Form.

| The kit contains | (A) One tablet of Rifampicin 150 mg (Enteric coated). |
| --- | --- |
|  | (B) One tablet containing Isoniazid, Ethambutol Hydrochloride and Pyrazinamide (Film coated). |

(A) Rifampicin Tablets 150 mg (Enteric Coated)

|  | Per tablet |
| --- | --- |
| Rifampicin | 225 mg |
| Microcrystalline Cellulose | 55 mg |
| Starch | 10 mg |
| Water | — |
| Magnesium Stearate | 5 mg |
| Sodium Lauryl Sulphate | 5 mg |

Pass Rifampicin and Microcrystalline Cellulose through sieve and granulate the mass with Starch paste and pass through multimill. Dry the granules at 50° to 60° C. and pass through sieve of mesh size 18. Pass Magnesium Stearate and Sodium Lauryl Sulphate through sieve of mesh size 60 and mix with the dried granules and compress.

Enteric Coating of Rifampicin Tablets (Batch Size 2.0 Kg)

| Eudragit L 100 | 80.00 g |
| --- | --- |
| Purified Talc | 25.00 g |
| Triethyl Citrate | 15.00 g |
| Dichloromethane | 1.30 L |
| Isopropyl Alcohol | 0.60 L |

Dissolve Eudragit L 100 in a Isopropyl Alcohol and Dichloromethane mixture. Add Triethyl Citrate and Talc to the above bulk and mix for 45 minutes. Coat the tablets to a weight build up of 4–6% w/w.

(B) Isoniazid, Ethambutol Hydrochloride and Pyrazinamide Tablets (Film Coated)

|  | Per Tablet |
| --- | --- |
| Pyrazinamide | 750 mg |
| Ethambutol Hydrochloride | 400 mg |
| Isoniazid | 150 mg |
| Magnesium Stearate | 15 mg |
| Talc | 6 mg |
| Starch | 35 mg |
| Sodium Starch Glycollate | 35 mg |
| Purified Water | — |

Pass Pyrazinamide, Ethambutol Hydrochloride and Isoniazid through a sieve and granulate with Starch paste prepared in Purified Water. Pass the wet mass was passed through multimill and dry the granules at 50–60° C. Pass the dried granules through sieve of mesh size 16. Pass Magnesium Stearate, Purified Talc and Sodium Starch Glycollate through sieve of mesh size 60 and mix with dried granules and compress.

Film Coating of Tablets (Batch Size 2.0 Kg)

| Hydroxypropyl Methylcellulose | 40.00 g |
| --- | --- |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hydroxypropyl Methylcellulose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

39. Isoniazid in Taste Masked Form Using Complexation

| Isoniazid | 1.0 Kg |
| --- | --- |
| Polystyrene Copolymer | 2.0 Kg |
| Water | 5.0 L |

Disperse Polystyrene copolymer in Water and add Isoniazid to it with constant stirring. Continue stirring for two hours and filter the complex and dry.

The above complex may be included in a tablet, capsule or suspension dosage form for taste masked and delayed release Isoniazid suspension containing other antitubercular drugs.

40. Microemulsion Formulation of Rifampicin and Other Tubercular Drugs.

|  | Per Tablet |
|---|---|
| Rifampicin | 150 mg |
| Pyrazinamide | 250 mg |
| Ethambutol Hydrochloride | 267 mg |
| Isoniazid | 100 mg |
| Poloxamer 188 | 25 mg |
| Vitamin E Polyethylene Glycol Succinate | 20 mg |
| Hydrogenated vegetable Oil | 20 mg |
| Magnesium Stearate | 15 mg |
| Talc | 6 mg |
| Starch | 35 mg |
| Sodium Starch Glycollate | 35 mg |
| Purified Water | — |

Pass Pyrazinamide, Ethambutol Hydrochloride, Rifampicin and Isoniazid through a sieve and granulate with Starch paste containing Poloxamer 188, Vitamin E Polyethylene Glycol Succinate and Hydrogenated vegetable oil. Pass the wet mass was passed through multimill and dry the granules at 50–60° C. Pass the dried granules through sieve of mesh size 16. Pass Magnesium Stearate, Purified Talc and Sodium Starch Glycollate through sieve of mesh size 60 and mix with dried granules and compress.

Such tablets on dilution with water gives a microemulsion.

41. Vesicular Carriers for Rifampicin

|  |  |
|---|---|
| Rifampicin | 500 mg |
| Chloroform | q.s. |
| Cholesterol | 49 mg |
| Polysorbate 80 | 35 mg |
| Distearyl Phosphatidyl Choline | 7 mg |
| Dichloromethane | 10 ml |
| Calcium Chloride (25 mM solution) | 10 ml |

Dissolve Rifampicin in minimum volume of Chloroform and add Cholesterol, Polysorbate 80 and Distearyl Phosphatidyl Choline to it. Add Dichloromethane, 2 ml of calcium Chloride solution. Sonicate for 2 hours or till a milky emulsion is formed and evaporate the solvent layer under controlled conditions of temperature and pressure on a rota evaporator till a semisolid viscous liquid is obtained. Now add remaining amount of Calcium Chloride solution and evaporate the solvents on a rota evaporator for overnight and collect the vesicular carriers.

Such carriers can be incorporated into a tablet, capsule or liquid dosage form.

42. Tablet Containing Rifampicin in Molecular Dispersion (in Delayed Release) Form.

|  | Per Tablet |
|---|---|
| Rifampicin in delayed release molecular dispersion Form equivalent to Rifampicin (as per example no. 9) | 225 mg |
| Pyrazinamide | 750 mg |
| Ethambutol Hydrochloride | 400 mg |
| Isoniazid | 150 mg |
| Lactose | 60 mg |
| Magnesium Stearate | 20 mg |
| Sodium Starch Glycollate | 30 mg |
| Starch | 20 mg |
| Purified Talc | 5 mg |
| Purified Water | — |

Pass Pyrazinamide, Ethambutol Hydrochloride, Isoniazid and Lactose through a sieve and granulate with Starch Paste prepared in Purified Water. Pass the wet mass through multimill and dry the granules at 50–60° C. Pass the dried granules through sieve of mesh size 16. Pass Magnesium Stearate, Purified Talc and Sodium Starch Glycollate through sieve of mesh size 60 and mix with dried granules and rifampicin delayed release powder. Compress the blend into tablets.

Film Coating of Tablets (Batch Size 2.0 Kg)

|  |  |
|---|---|
| Hypromellose | 40.00 g |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

43. Tablet Containing Isoniazid in Molecular Dispersion (in Delayed Release) Form.

|  | Per Tablet |
|---|---|
| Isoniazid in delayed release molecular dispersion form equivalent to Isoniazid (as per example no. 23) | 150 mg |
| Pyrazinamide | 750 mg |
| Ethambutol Hydrochloride | 400 mg |
| Rifampicin | 225 mg |
| Lactose | 60 mg |
| Magnesium Stearate | 20 mg |
| Sodium Starch Glycollate | 30 mg |
| Starch | 20 mg |
| Purified Talc | 5 mg |
| Purified Water | — |

Pass Pyrazinamide, Ethambutol Hydrochloride, Rifampicin and Lactose through a sieve and granulate with Starch Paste prepared in Purified Water. Pass the wet mass through multimill and dry the granules at 50–60° C. Pass the dried granules through sieve of mesh size 16. Pass Magnesium Stearate, Purified Talc and Sodium Starch Glycollate through sieve of mesh size 60 and mix with dried granules and isoniazid delayed release powder. Compress the blend into tablets.

Film Coating of Tablets (Batch Size 2.0 Kg)

| | |
|---|---|
| Hypromellose | 40.00 g |
| Purified Talc | 2.00 g |
| Polyethylene Glycol 400 | 8.00 g |
| Titanium Dioxide | 2.00 g |
| Colour | q.s. |
| Dichloromethane | 0.66 L |
| Isopropyl Alcohol | 0.33 L |

Dissolve Hypromellose in Isopropyl Alcohol and Dichloromethane mixture. Add Polyethylene Glycol 400, Titanium Dioxide, Purified Talc and colour to the above bulk and mix for 45 minutes. Coat the tablets to a weight build up of 3–4% w/w.

The invention claimed is:

1. An oral pharmaceutical composition comprising: rifampicin and isoniazid, formulated so that the release of rifampicin and isoniazid takes place at separate locations inside the gastrointestinal tract and so that after release the rifampicin and isoniazid do not contact each other in the solution state, and wherein the rifampicin is formulated to release in the stomach and the isoniazid is formulated in an extended or delayed enteric release form.

2. The composition of claim 1, wherein delayed release of isoniazid is achieved by treating isoniazid with one or more pH sensitive polymers.

3. The composition of claim 2, wherein the pH sensitive polymers are selected from cellulose acetate phthalate, hydroxypropyl methylcellulose phthalate, polyvinyl acetate phthalate, hydroxypropyl methylcellulose acid succinate, alginic acid, methacrylic acid polymers, carbomers, polacrillin potassium, and chitosan.

4. The composition of claim 1, wherein isoniazid, is present in form of molecular dispersion along with a pH sensitive polymer resulting in delayed release of the drug.

5. The composition of claim 1, wherein extended release of isoniazid is achieved by treating isoniazid with one or more pH independent polymers.

6. The composition of claim 5, wherein the pH independent polymers are selected from cellulose, hydroxypropyl methylcellulose, hydroxypropyl cellulose, hydroxyethyl cellulose, ethyl cellulose, xanthan gum, karaya gum, guar gum, tragacanth and acacia.

7. The composition of claim 1, which is dispensed in kit form wherein the drugs are present in individual compressed unit dosage forms.

8. The composition of claim 1, wherein rifampicin or isoniazid, or both, are present in micronized form.

9. The composition of claim 1, comprising crystal forms of rifampicin or isoniazid, or both.

10. The pharmaceutical composition of claim 1, further comprising at least one other anti-tubercular drug.

11. The pharmaceutical composition of claim 1 in the form of a tablet, capsule, suspension, pastille, jellies or powder.

12. The pharmaceutical composition of claim 11 in the form of a film coated tablet, compression coated tablet or bilayer tablet.

13. The pharmaceutical composition of claim 1, wherein the isoniazid or rifampicin or both are present in taste masked form.

14. A process for the preparation of an oral pharmaceutical composition comprising rifampicin and isoniazid, which is formulated so that the release of rifampicin and isoniazid takes place at separate locations inside the gastrointestinal tract and so that the contact of rifampicin and isoniazid with each other in solution state is prevented, and wherein the rifampicin is formulated to release in the stomach and the isoniazid is formulated in an extended or delayed enteric release form.

15. The process of claim 14, wherein delayed release of isoniazid is achieved by treating isoniazid with one or more pH sensitive polymers.

16. The process of claim 15, wherein the pH sensitive polymers are selected from cellulose acetate phthalate, hydroxypropyl methylcellulose phthalate, polyvinyl acetate phthalate, hydroxypropyl methylcellulose acid succinate, alginic acid, methacrylic acid polymers, carbomers, polacrillin potassium, and chitosan.

17. The process of claim 14, wherein isoniazid, is present in form of molecular dispersion along with a pH sensitive polymer resulting in delayed release of the drug.

18. The process of claim 14, wherein extended release of isoniazid is achieved by treating isoniazid with one or more pH independent polymers.

19. The process of claim 18, wherein the pH independent polymers are selected from cellulose, hydroxypropyl methylcellulose, hydroxypropyl cellulose, hydroxyethyl cellulose, ethyl cellulose, xanthan gum, karaya gum, guar gum, tragacanth and acacia.

20. The process of claim 14, where rifampicin or isoniazid, or both, are present in micronized form.

21. The process of claim 14, wherein the composition comprises crystal forms of rifampicin or isoniazid or both.

22. The process of claim 14, wherein the composition comprises isoniazid or rifampicin or both in taste masked form.

* * * * *

UNITED STATES PATENT AND TRADEMARK OFFICE
CERTIFICATE OF CORRECTION

| | | |
|---|---|---|
| PATENT NO. | : 7,195,769 B2 | Page 1 of 2 |
| APPLICATION NO. | : 10/110134 | |
| DATED | : March 27, 2007 | |
| INVENTOR(S) | : Amarjit Singh et al. | |

It is certified that error appears in the above-identified patent and that said Letters Patent is hereby corrected as shown below:

Column 8, line 1, "2. Dissolve Rifampicin was dissolved in Dichloromethane"
    should read -- 2. Dissolve Rifampicin in Dichloromethane --;
        line 3, "3. Evaporate the solvents on a water bath and pass the"
    should read -- 3. Evaporate the solvents on a water bath and pass the residue --.

Column 12, line 7, add Table heading -- Core tablet       Per tablet --.

Column 13, line 54, "Dioxide, Purified Tale and colour to the above bulk and mix"
    should read -- Dioxide, Purified Talc and colour to the above bulk and mix --.

Column 16, line 54, add Table heading, -- Outer tablet --.

Column 17, line 26, add Table heading, -- Per tablet --.
    line 61, add Table heading, -- Per tablet --.

Column 19, line 46, "Delayed Release Form."
    should read -- Delayed Release Form. Each 10ml of reconstituted suspension
               contains: --.

Column 20, line 2, "Delayed Release Form."
    should read -- Delayed Release Form. Each 10ml of reconstituted suspension
               contains: --.

Column 22, line 31, "prepared in Purified Water. Pass the wet mass was passed"
    should read -- prepared in Purified Water. Pass the wet mass --.

UNITED STATES PATENT AND TRADEMARK OFFICE
CERTIFICATE OF CORRECTION

PATENT NO. : 7,195,769 B2
APPLICATION NO. : 10/110134
DATED : March 27, 2007
INVENTOR(S) : Amarjit Singh et al.

It is certified that error appears in the above-identified patent and that said Letters Patent is hereby corrected as shown below:

Column 23, line 23, "wet mass was passed through multimill and dry the granules" should read -- wet mass through multimill and dry the granules --.

Signed and Sealed this

Twenty-ninth Day of April, 2008

JON W. DUDAS
*Director of the United States Patent and Trademark Office*